(12) United States Patent
Am Ende et al.

(10) Patent No.: US 6,558,435 B2
(45) Date of Patent: May 6, 2003

(54) REACTIVE CRYSTALLIZATION METHOD TO IMPROVE PARTICLE SIZE

(75) Inventors: David J. Am Ende, Waterford, CT (US); Thomas C. Crawford, Essex, CT (US); Neil P. Weston, Groton, CT (US)

(73) Assignees: Pfizer, Inc., New York, NY (US); Pfizer Products, Inc., Groton, CT (US)

(*) Notice: Subject to any disclaimer, the term of this patent is extended or adjusted under 35 U.S.C. 154(b) by 0 days.

(21) Appl. No.: 09/863,492

(22) Filed: May 23, 2001

(65) Prior Publication Data

US 2002/0016498 A1 Feb. 7, 2002

Related U.S. Application Data

(60) Provisional application No. 60/207,629, filed on May 26, 2000.

(51) Int. Cl.$^7$ .......................... B01D 9/00; C07D 419/00
(52) U.S. Cl. .................... 23/300; 544/284; 546/272.4
(58) Field of Search .................. 23/295 R, 300; 544/230, 284; 546/276, 272.4

(56) References Cited

U.S. PATENT DOCUMENTS

| | | | | |
|---|---|---|---|---|
| 4,675,194 A | * | 6/1987 | Gaffney | 426/39 |
| 4,788,011 A | * | 11/1988 | Busse et al. | 260/507 |
| 5,143,965 A | * | 9/1992 | Mertz | 524/436 |
| 5,314,506 A | | 5/1994 | Midler, Jr. et al. | 23/295 |
| 5,830,418 A | | 11/1998 | Konig et al. | 422/245.1 |
| 5,853,691 A | | 12/1998 | Doxsee | 423/491 |

FOREIGN PATENT DOCUMENTS

| | | | |
|---|---|---|---|
| CH | 671166 | 8/1989 | B01D/9/02 |
| EP | 0275607 | 7/1988 | B02C/19/18 |
| EP | 0461930 | 12/1991 | B01D/9/00 |
| WO | WO 9823350 | 6/1998 | B01D/9/00 |

* cited by examiner

Primary Examiner—Mukund J. Shah
Assistant Examiner—Zachary C. Tucker
(74) Attorney, Agent, or Firm—Scully, Scott, Murphy & Presser

(57) ABSTRACT

This invention provides a method of conducting a simultaneous chemical reaction and controlled crystallization of the product employing impinging fluid jet streams containing reactants capable of producing the product with desired particle size characteristics.

27 Claims, 2 Drawing Sheets

REACTIVE CRYSTALLIZATION METHOD TO IMPROVE PARTICLE SIZE

This application claims the benefit of U.S. provisional application Ser. No. 60/207,629, filed May 26, 2000.

This invention relates to a method for simultaneously synthesizing a compound and isolating the product in a crystallization procedure, which controls particle size.

U.S. Pat. No. 5,314,506, incorporated herein by reference, provides a method of impinging fluid jet streams in a continuous crystallization process to achieve high intensity micromixing of fluids so as to form a homogeneous composition prior to the start of nucleation. This process permits direct crystallization of the high surface area particles of high purity and stability. Particle size may be controlled by varying the concentration of solutions, temperature and velocity of the solution through the jets. With this method it is possible to prepare compounds of 5 to 1000 microns.

WO 00/44468, incorporated herein by reference, describes an apparatus and process for crystallizing submicron-sized particles with the introduction of a sonication probe with impinging jets.

The use of an impinging jet device optionally with a sonication probe to achieve high intensity mixing coupled with a chemical reaction to provide a new chemical compound of controlled particle size of crystalline materials is novel.

SUMMARY OF THE INVENTION

The present invention provides a method for preparation and crystallization of pharmaceutical compounds or their intermediates which directly produces high surface area end product crystals with greatly improved stability and purity and thereby eliminates the need for subsequent high intensity milling to meet bioavailability requirements. By removing the need for milling, the novel jet process avoids associated problems of noise and dusting, cuts yield loss, and saves the time and extra expense incurred during milling. It also removes an extra opportunity for personnel contact with a highly potent pharmaceutical agent, or for adverse effects on labile compounds. The small particle size attained with the jet process is consistent within a single run and is reproducible between runs. Reproducibility is an attribute of this process that is not common to "reverse addition" methods typically used to produce small crystals.

The pure, high surface area particles that result from the jet process also display superior crystal structure when compared to particles formed via standard slow crystallization plus milling methods using the same quality and kind of feed compound. Improvements in crystal structure result in decreases in decomposition rate and therefore longer shelf life for the crystallized product or a pharmaceutical composition containing the crystallized material.

This invention provides a process for preparation and crystallization of a chemical compound in a continuous process.

More particularly, this invention relates to the use of impinging jets to achieve high intensity micromixing of solvents containing chemical reactants so as to produce a chemical reaction which forms a reaction product under high supersaturation conditions leading to a rapid nucleation in a continuous reaction and crystallization process.

Nucleation and precipitation can be initiated by utilizing the effect of temperature reduction on the solubility of the compound to be crystallized in a particular solvent (thermoregulation), or by taking advantage of the solubility characteristics of the compound in solvent mixtures, or by some combination of the two techniques. Further, the product of the reaction will usually be highly insoluble in the final solvent or combination of solvents.

The novel process of this invention provides for the direct crystallization of high surface area particles of high purity and stability.

This invention provides a process for synthesis and crystallization of a chemical compound comprising contacting one or more jet streams of a solution in a first solvent of a first reactive intermediate and one or more jet streams of a solution in a second solvent of a second reactive intermediate, said jet streams impinging to crate high turbulence at their point of impact under conditions of temperatures and pressure which permit reaction of said first and second reactive intermediates to produce a product; and selecting said first and second solvents so that said product is of limited solubility in a mixture of said first and second solvents; and said jet streams impinging to create high turbulence at their point of impact and each jet stream having sufficient linear velocity to achieve high intensity micromixing of said solutions followed by reaction of first and second reactive intermediates, followed by nucleation of said product and production of small crystals of controlled particle size.

In another aspect, this invention also provides a process wherein one of said first or second reactive intermediates is a basic intermediate and the other intermediate is an acidic intermediate.

In another aspect, this invention also provides a process wherein one of said first or second reactive intermediates is a zwitterion and the other intermediate is an acid. This invention further provides a process wherein one of said first or second reactive intermediates is a zwitterion and the other intermediate is a base.

In another aspect, this invention also provides a process wherein one of said first or second reactive intermediates is an organic salt form and the other intermediate is a neutralizing acid compound.

In another aspect, this invention also provides a process wherein one of said first or second reactive intermediates is an organic salt form and the other intermediate is a neutralizing basic compound.

This invention also provides a process, wherein said synthesis results in the forming or breaking of a covalent bond and wherein the product or its corresponding salt form crystallizes.

This invention also provides a process wherein said first solution is a pharmaceutical salt form solution and said second solution is a solution containing either an acid or a base. For example, a solution of Voriconazole camphorsulfonate may be reacted with a solution of sodium acetate to produce Voriconazole free base with controlled particle size. Such a reaction is known as free-basing or conversion to the free base. The process also applies to the conversion to free acids by treating a pharmaceutical salt form with acid to form the free acid. Salt forms include, but are not limited to, those compounds containing anions such as hydrochloride, acetate, besylate, citrate, hydrobromide, D or L lactate, mesylate, succinate, camphorsulfonate, sulfate, D or L tartrate, stearates, tosylates, and cations such as calcium, potassium, sodium and ethylenediamine.

In another aspect, this invention provides a process wherein said chemical compound to be formed is a pharmaceutically acceptable salt form with an ion component selected from the group consisting of: hydrochloride, acetate, besylate, citrate, hydrobromide, D or L lactate, mesylate, succinate, sulfate, D or L tartrate, stearate, tosylate; a cation selected from calcium, potassium and sodium; and ethylenediamine.

In one aspect, the invention provides a process wherein said chemical compound to be formed is Ziparasidne hydrochloride monohydrate. In another aspect, this invention provides a process wherein one reactive intermediate is Ziprasidone free base and the other reactive intermediate is an aqueous hydrochloric acid solution.

In another aspect, the invention proves a process wherein said product to be formed is Voriconazole free base. In a further aspect, this invention provides a process wherein the basic intermediate is selected from, but not limited to, sodium acetate, potassium acetate, sodium hydroxide, potassium hydroxide, sodium carbonate, sodium bicarbonate, and said acidic intermediate is Voriconazole R-(−)-camphorsulfonic acid salt.

In another aspect, this invention provides a process wherein the compound to be crystallized is 5,8,14-triazatetracyclo[$10.3.1.0^{2,11}.0^{4,9}$]-hexadeca-2(11),3,5,7,9-pentaene L-tartrate. Further, the invention relates to a process wherein the first reactive intermediate is the 5,8,14-triazatetracyclo[$10.3.1.0^{2,11}.0^{4,9}$]-hexadeca-2(11),3,5,7,9-pentaene free base and the second reactive intermediate is L-tartaric acid.

In another aspect, this invention provides a process wherein the desired product is in the form of crystalline aggregates which are of controlled size. In another aspect the invention provides a process wherein the linear velocity of jet streams is at least 5 m/sec. In a further aspect, the invention provides a process wherein said product is solvated. In another aspect, this invention provides a sonication probe along with impinging jets to achieve high intensity micromixing.

BRIEF DESCRIPTION OF THE DRAWINGS

An embodiment of the invention has been chosen for purposes of illustration and description, and is shown in the accompanying drawings forming a part of the specification wherein.

Figure 1:
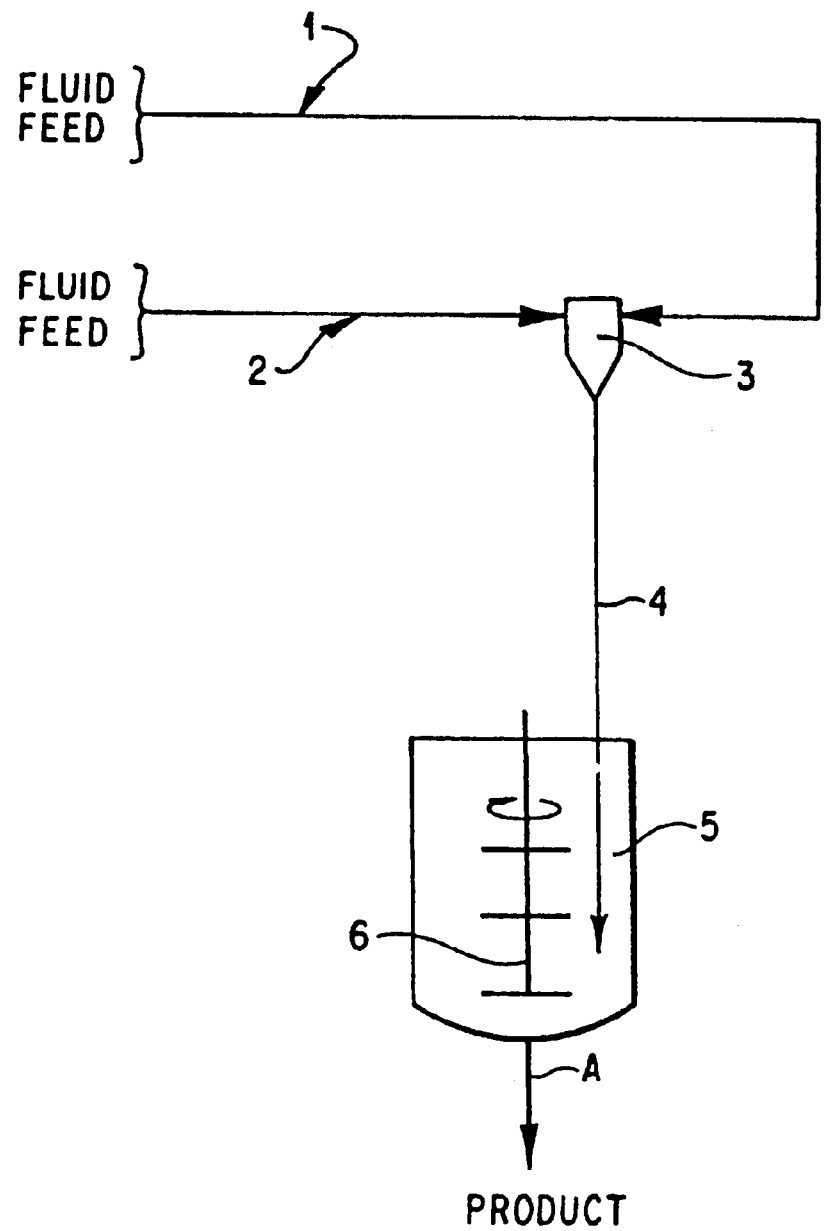
FIG. 1 is a schematic diagram showing a crystal production system depicting the jet chamber 3, the transfer line 4, the stirred vessel 5, the agitation device 6 and the entry point of two fluids 1 and 2 into the system.

After micromixing in a jet chamber, the material leaves the jet chamber as depicted in FIG. 1, travels into a stirred vessel 5 either directly or via a transfer line 4, and after an appropriate age time, the product suspension flows out of the vessel as indicated by arrow A.

Figure 2:
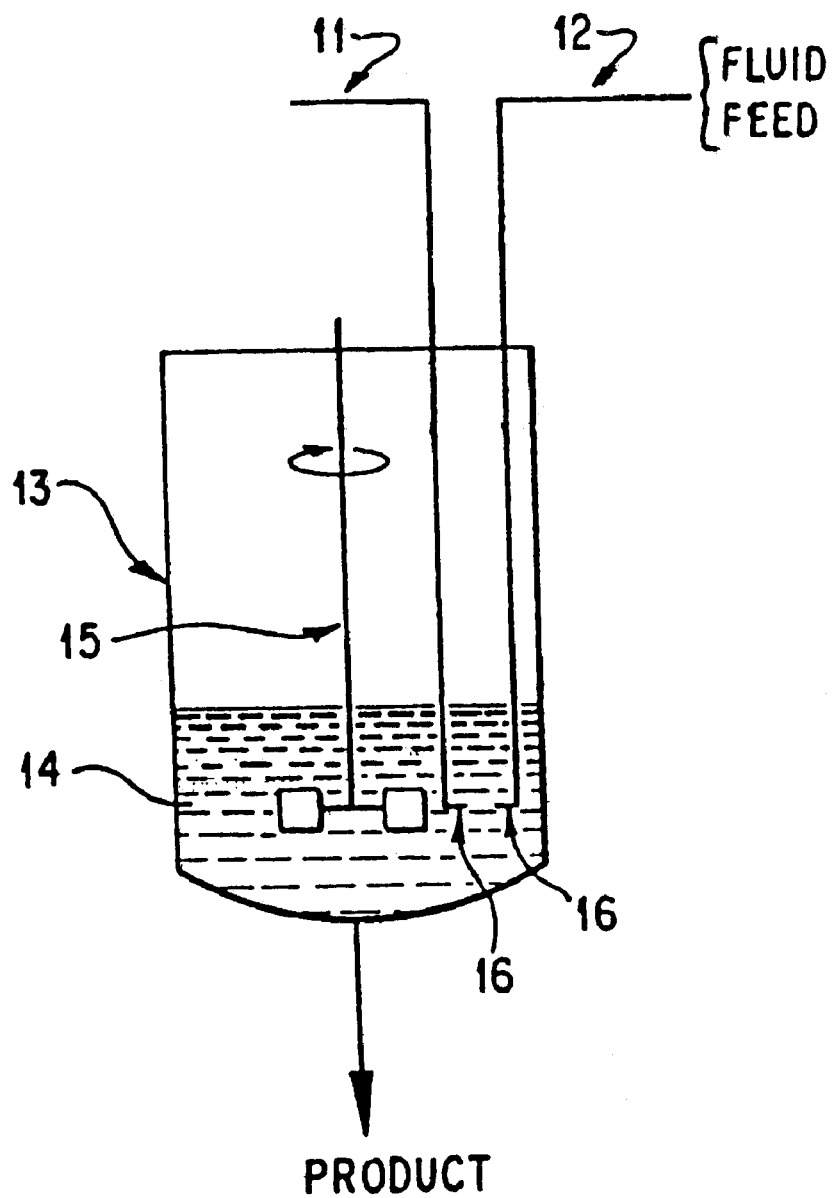

In another embodiment, shown in FIG. 2, two fluids 11 and 12 enter directly into the stirred vessel 13 containing a liquid 14 which is a solvent or antisolvent or mixture thereof where the jets 16 emit fluid jet streams that impinge and micromix near the effluent stream of the impeller 15.

DETAILED DESCRIPTION OF THE INVENTION

The novel process of this invention involves the use of jets to create impinging fluid jet streams and thereby achieve high intensity micromixing and reaction of the fluids prior to nucleation in a crystallization process. Two or more jets may be used to micromix two or more fluids. Preferably, two jets are used to micromix two fluids. When using two jets, preferably the two impinging jet streams should be substantially diametrically opposed to each other, i.e., they should be at or close to a 180 degree angle to each other from an overhead view. FIG. 1 shows one embodiment of this invention wherein two jets are employed; fluids 1 and 2 enter the jet chamber 3 where micromixing takes place.

Regardless of the number of jets used, the jet nozzles should be placed so that the fluid streams they emit will impinge, either inside the jet chamber or directly in the stirred vessel. The fluid jets must impinge to create an immediate high turbulence impact; concentric or converging jets generally create insufficient turbulence to achieve the required micromixing. When two jets are used with a jet chamber, as show in FIG. 1, the two jet nozzles are preferably arranged so that they are substantially diametrically opposed to each other with their outlet tips directed to face each other; i.e., the two jet nozzles are at or close to a 180 degree angle to each other from an overhead view. Preferably, each jet outlet nozzle can have a slight downward angle from the horizontal of about 10 degrees to help the flowing material move down and out of the chamber.

Likewise, two jet nozzles placed directly inside the stirred vessel are preferably arranged so that they are substantially diametrically opposed to each other with their outlet tips directed to face each other. When the jet nozzles are so placed, each nozzle can have a slight upward or downward angle from the horizontal of from 0 degrees up to about 15 degrees, but preferably the two nozzles have just enough downward angle from the horizontal (ca. 13 degrees) to ensure that the fluid stream of one will not enter the outlet hole of the opposite nozzle, possibly causing crystallization in the jet. The use of a sonication probe along with impinging jets aids in achieving high intensity micromixing in a continuous process.

One jet nozzle is used to transport one of the two fluids from an external source into the chamber and the other jet is used to similarly transport the other fluid. The distance between the nozzle tips inside the jet chamber or stirred vessel should be such that the hydrodynamic form of each fluid jet stream remains essentially intact up to the point of impingement. Therefore, the maximum distance between the nozzle tips will vary depending on the linear velocity of the fluids inside the jet nozzles. To obtain good results for generally nonviscous fluids, linear velocity in the jet nozzles should be at least about 5 meters/sec., more preferably above 10 meters/sec., and most preferably between about 20 to 25 meters/sec., although the upper limit of linear velocity is only limited by the practical difficulties involved in achieving it. Linear velocity and flow rate can both be controlled by various known methods, such as altering the diameter of the entry tube and/or that of the nozzle outlet, and/or varying the strength of the external force that moves the fluid into and through the nozzle. Each jet apparatus can be manipulated independently to attain a desired final fluid composition ratio. When the desired flow ratio of one jet to the other differs from unity, preferably the difference is compensated for by appropriate sizing of the entry tubes. For example, if a 4:1 volumetric ratio of feed solution to anti-solvent is desired, the entry tube delivering feed solution should be twice the diameter of the entry tube delivering anti-solvent. When the jet streams impinge inside a jet chamber, residence time for the fluid inside the jet chamber is typically very short, i.e., less than ten seconds.

A transfer line 4 as shown in FIG. 1 may or may not be used to deliver the fluid mixture into a stirred vessel 5 from the jet chamber. Solvent, anti-solvent or mixtures thereof optionally containing seed and optionally heated to attain optimum results can be put inside the stirred vessel at the start of the process before the micromixed fluids enter the stirred vessel; this technique is especially preferred when the jet streams impinge directly in the stirred vessel. Crystal digestion (Ostwald ripening, improvement of surface structure) takes place inside the stirred vessel.

Solvents used in this invention are preferred to be miscible. The first solvent and second solvent may be identical provided that the ultimate product has limited solubility in the common solvent.

In the usual case, the first and second solvents are not identical, the first solvent being adapted to dissolve one reactive intermediate and the second solvent the second reactive intermediate. At least one of the solvents should be an "anti-solvent" which is chosen for its relatively low solvation properties with respect to the product. Although this invention has been exemplified for preparing and crystallizing pharmaceutical salts, it will be obvious to those skilled in this art that the process described herein is applicable to prepare many types of small molecules with controlled particle size. The process is particularly useful for single step reactions, which proceed at a high rate under moderate conditions, for example, salt-formations, free-basing and nucleophilic reactions.

In the present invention, in certain cases, first and second solvents can be identical. This has been demonstrated and applies when both, first and second reactive intermediates are soluble in said solvent but whose reaction product or resulting salt form is highly insoluble in said solvent. In this case, the solvent acts as both the solvent and antisolvent for the reactive crystallization process.

The following examples are given for the purpose of illustrating the present invention and should not be construed as limitations on the scope or spirit of the present invention.

EXAMPLES

Example 1

Reaction and Crystallization of Ziprasidone to Achieve Desired Salt Form

Ziprasidone (CAS-138982-67-9) free base (3.7 grams) was dissolved into 200 ml (55 volumes) of tetrahydrofuran (THF) in a 250 ml 3-neck round bottom flask and heated to reflux at 65° C. for 20 minutes. The solution was hot filtered through a glass sintered Buchner funnel. The saturated solution was added to a 2L jacketed glass vessel preheated to a jacket temperature of 80° C. and equipped with reflux condenser. The bottom outlet of this vessel is connected to a pump where the liquid is pumped to a 1/16 OD jet nozzle (0.02 inch ID). 200 ml of an aqueous 0.8 wt % HCl solution is added to a second 2L jacketed vessel held at 25° C. The bottom outlet of the second vessel is plumbed to a second 1/16 OD jet nozzle (0.02 inch ID). The jets were secured inside a 1 liter jacketed receiver vessel and were diametrically opposed to each other with approximately 1 cm of distance between the two jets such that the liquid streams meet at a point of impingement to create a vertical impingement film. The 1-liter jacketed receiving vessel was held at 20° C. and was empty at the start of the run. The impinging jets were started with flow rates of 120 ml/min for the THF solution and 115 ml/min for the HCl solution. Linear velocities were 9.9 m/sec and 9.5 m/sec for the THF and HCl solutions respectively. The solution slurry was collected in the receiver vessel with the volume level eventually rising above the jets. A Rushton turbine impeller at 200 rpm was used in the receiver to provide mixing. The slurry was allowed to age for 36 minutes. The crystals were filtered and washed with 150 ml of Dl water and dried in a crystallizing dish over night.

X-ray diffraction (XRD) and differential scanning calorimetry (DSC) indicated the correct form of Ziprasidone hydrochloride monohydrate was produced by the impinging jet reactive crystallization process. The dried powder crystals were sieved through a 600 micron sieve as a means to delump. The particles were analyzed by Malvern using hexane as a dispersant. The particle size results indicated that 90% of the particles, $D_{90}$, by volume were less than 83 microns while the volume mean diameter, $D[4,3]$, was 43 microns. No particles with diameters of less that 0.9 micron were detected indicating that fines were not produced.

Example 2

Reaction and Crystallization of Ziprasidone to Achieve Desired Salt Form to Obtain Preferred Particle Size The reaction crystallization of example 1 as conducted with the following modifications: 60 volumes of THF were used relative to Ziprasidone free base. The temperature of the Ziprasidone free base in THF solution as maintained at 60° C. No hot filtration was performed prior to preparing the Ziprasidone solution in the 2L vessel. The aqueous HCl solution was maintained at 15° C. while the receiving vessel was held at 30° C. The flow rates for the Ziprasidone free base solution in THF and the aqueous HCl solution were 120 ml/min and 100 ml/min respectively and were run for 3 minutes. The age time for the crystals was 2 minutes. The crystals were vacuum filtered, washed with 160 ml Dl water, and air dried.

XRD and DSC indicated that the correct form of Ziprasidone HCl salt was produced by the reactive crystallization process. The crystals were sieved through a 600 micron sieve to delump and the particles were analyzed by Malvern using hexane as a dispersant. The particle size results indicated that 90% of the particles by volume were less than 41 microns while the volume mean diameter, $D[4,3]$, was 22.5 microns. No particles of less that 1.0 micron were detected indicating that fines were not produced. According to patent EU 0 965 343 A2 (08.06.1999), the most preferred mean particle size of Ziprasidone hydrochloride monohydrates is in the 5–30 micron range obtained through milling operations which the present invention achieves without the need for high intensity milling. The particle sizes stipulated herein and in the claims refer to particle sizes determined with Malvern light scattering.

In a comparative 15.6 kg sample produced by the typical batch crystallization process method followed by milling using a pin mill at 10,000 rpm, the volume mean diameter, $D[4,3]$, was 23.6 microns with 90% of the particles by volume less than 51 microns, while 5.4% of the batch by the volume distribution had particle size less than 1 micron indicating a much greater number of fines. The impinging jet produced reaction crystallization material, in both examples 1 and 2, showed a narrower particle size distribution with fewer fines produced while eliminating the milling operation.

Example 3

Reaction and Crystallization of Ziprasidone to Achieve Desired Salt Form but with Larger Particle Size The reaction crystallization of example 1 was modified to demonstrate ability to selectively control and achieve a larger particle size distribution. The modifications to example 1 were: a) 3.1 g of Ziprasidone free base dissolved in 65 volumes of THF was used, b) not hot filtration was performed in preparing the Ziprasidone free base THF solution, and c) the age time for the resulting crystals, after the impingement period, was 55 minutes prior to filtration. The crystals were vacuum filtered, washed with 150 ml of deionized water, and air dried. The dry Ziprasidone hydrochloride monohydrate particles were free flowing. Microscopy revealed the formation of a uniform distribution of crystalline aggregates that give superior filtration and powder properties such as flowability. Thus this method can influence degree of aggregation and provide benefits to bulk handling characteristics. The powder was not sieved prior to Malvern light scattering as it required no delumping. The volume mean particle size, D[4,3], was 104 micron with 90% by volume, $D_{90}$, less than 210 microns. No particles below 1 micron were measured, indicating no fines were produced.

Example 4

Reaction-Crystallization of Voriconazole Camphorsulfonic Acid Salt to Voriconazole Free Base (U.S. Pat. No. 5,567,817; CAS-1378234-62-9)

28.75 g of Voriconazole R-(-)-camphorsulfonic acid salt was dissolved in 120 ml of a 50:50 volume ratio of ethanol and deionized water and placed in a 2L jacketed vessel equilibrated at 30° C. 4 liters of an aqueous solution of sodium acetate (3.4 wt %) was placed in a stainless steel pressure can at room temperature and pressurized to 26 psig with nitrogen. Each vessel was plumbed to individual jets assembled in a chamber similar to the configuration depicted in FIG. 1. The jets were 1/16 inch OD and 0.02 inch ID. The flow of sodium acetate solution was started through the jet at 115 ml/min, controlled via the nitrogen pressure. The Voriconazole camphorsulfonic acid salt solution was then turned on with flow rate of 115 ml/min through the jet. The flow of the two solutions created at impingement zone between the two jets and while crystalline material was observed to be forming in the impingement chamber which flowed down to the receiving vessel that was equilibrated to 5° C.

The jets were run until the Voriconazole salt solution was consumed. The slurry was aged for 10 minutes then vacuum filtered, and washed with 70 ml D1 water.

The crystals were dried in a vacuum oven at 50° C. and 10 inches of Hg with an air bleed for 24 hours. The dried material was sieved through a 30 mesh (600 µm) screen as a means to delump. Differential scanning calorimetry and x-ray diffraction confirmed the complete conversion to the Voriconazole free-base. No unreacted Voriconazole camphorsulfonate was detected.

Dry particle sizing analysis (SympaTec) revealed a volume mean diameter of 22 microns with 90% of particles (D[v,0.9]) less than 41 microns and 50% of particles (D[v, 0.50]) less than 18 microns. Specification of product conventionally obtained by jet milling is 90% less than 130 microns and 50% less than 50 microns.

Example 5

Reactive Crystallization of 5,8,14-triazatetracyclo [$10.3.1.0^{2,11}.0^{4,9}$]-hexadeca-2-(11),3,5,7,9-pentaene to Achieve Desired Salt Form and Particle Size Using Submerged Impinging Jets 1.006 grams of 5,8,14-triazatetracyclo[$10.3.1.0^{2,11}.0^{4,9}$]-hexadeca-2(11),3,5,7,9-pentaene free base was dissolved in 30 ml of ethyl acetate and 5 mL of methanol in a conical shaped centrifuge tube and held at room temperature. In a separate conical shaped centrifuge tube 0.96 g of (L)-tartaric acid was dissolved in 40 mL methanol at room temperature.

A receiving vessel contained 250 ml of methanol and 250 ml of ethyl acetate to which 20 milligrams of jet milled 5,8,14-triazatetracyclo[$10.3.1.0^{2,11}.0^{4,9}$]-hexadeca-2(11),3, 5,7,9-pentaene (L)-tartrate were added as seed. The seed had a volume mean diameter of 2.7 microns. The receiver was equipped with magnetic stirrer to suspend the seed in the methanol-ethyl acetate solvent system. The impinging jet apparatus was submerged in the receiver vessel with both jets having inside diameters of 0.007 inches (ID).

Flow of neat methanol and ethyl acetate was initiated through their respective jets at 20 ml/min for 5 seconds from separate reservoirs to establish steady state flow. By way of two 3-way valves the solutions of 5,8,14-triazatetracyclo [$10.3.1.0^{2,11}.0^{4,9}$]-hexadeca-2(11),3,5,7,9-pentaene free base solution and (L)-tartaric acid were switched on so they would impinge each other at the same 20 ml/min flow rate. The velocities through the jets were 13.4 meters/sec. After 1 minute of impingement the flows were stopped and the resulting slurry was allowed to age in the agitated receiver for 5 minutes. The slurry was vacuum filtered and dried at 40° C. overnight and delumped through a 500 micron sieve. Polymorph characterization by x-ray diffraction revealed it to be of the desired polymorphic form. Particle size analysis (Aerosizer) resulted in a volume mean diameter of 10 microns with narrow particle size distribution: 5% of particles were less than 5 microns and 95% of the particle were less than 15 microns.

What is claimed is:

1. A process for synthesis and crystallization of a pharmaceutical compound comprising:

contacting one or more liquid jet streams of a solution in a first solvent of a first reactive intermediate and one or more liquid jet streams of a solution in a second solvent of a second reactive intermediate, with each jet stream of said first reactive intermediate substantially diametrically opposite a jet stream of said second reactive intermediate and each jet stream of said second reactive intermediate substantially diametrically opposite a jet stream of said first reactive intermediate when viewed from overhead, so that each jet stream of said first reactive intermediate is directed into a jet stream of said second reactive intermediate and each jet stream of said second reactive intermediate is directed into a jet stream of said first reactive intermediate, such that the liquid streams meet at a point of impingement to create a vertical impingement film and with said jet streams creating turbulence at their point of impact under conditions of temperature and pressure which permit reaction of said first and second reactive intermediates to produce a product; and selecting said first and second solvents so that said product is insoluble in a mixture of said first and second solvents; and with each jet stream having sufficient linear velocity to achieve micromixing of said solutions followed by reaction of first and second reactive intermediates, followed by nucleation of said product and production of high surface area crystals of said product that meet bioavailability requirements.

2. The process of claim 1, wherein one of said first and second reactive intermediates is a basic intermediate and the other intermediate is an acidic intermediate.

3. The process of claim 1, wherein one of said first and second reactive intermediates is a zwitterion and the other intermediate is an acid.

4. The process of claim 1, wherein one of said first and second reactive intermediates is a zwitterion and the other intermediate is a base.

5. The process of claim 1, wherein one of said first and second reactive intermediates is an organic salt form and the other intermediate is a neutralizing acid compound.

6. The process of claim 1, wherein one of said first and second reactive intermediates is an organic salt form and the other intermediate is a neutralizing basic compound.

7. The process of claim 1, wherein said product is a pharmaceutically acceptable salt selected from the group consisting of hydrochloride, acetate, besylate, citrate, hydrobromide, D or L lactate, mesylate, succinate, sulfate, D or L tartrate, stearate, tosylate, calcium, potassium, sodium and ethylenediamine.

8. The process of claim 1, wherein said product further comprises aggregates of said high surface area crystals.

9. The process of claim 2, wherein one reactive intermediate is Ziprasidone free base and the other reactive intermediate is aqueous HCl solution.

10. The process of claim 1, wherein said product is Ziprasidone hydrochloride monohydrate.

11. The process of claim 1, wherein said product is Voriconazole free base.

12. The process of claim 2, wherein said basic intermediate is selected from sodium acetate, potassium acetate, sodium hydroxide, potassium hydroxide, sodium carbonate, sodium bicarbonate, and said acidic intermediate is Voriconazole R-(−)-camphorsulfonic acid salt.

13. The process of claim 1, wherein each of said liquid jet streams emerges from a nozzle having an outlet hole and with each said nozzle from which each jet stream emerges directed sufficiently downward to ensure that said liquid jet streams emerging from each nozzle will not enter said outlet hole of said substantially diametrically opposite nozzle.

14. The process of claim 1, wherein said product produced upon crystallization is solvated.

15. The process of claim 2, wherein one reactive intermediate is 5,8,14-triazatetracyclo[$10.3.1.0^{2,11}.0^{4,9}$]-hexadeca-2(11),3,5,7,9-pentaene free base and the other reactive intermediate is a L-tartaric acid solution.

16. The process of claim 1, wherein said product is 5,8,14-triazatetracyclo[$10.3.1.0^{2,11}.0^{4,9}$]-hexadeca-2(11),3,5,7,9-pentaene (L)-tartrate.

17. The process of claim 1, wherein the linear velocity of the jet streams is at least 5 m/sec.

18. The process of claim 1, wherein a sonication probe is included with said impinging jet streams.

19. A process for synthesis and crystallization of a pharmaceutical compound comprising contacting one or more jet streams of a solution in a first solvent of a first reactive intermediate and one or more jet streams of a solution in a second solvent of a second reactive intermediate, said jet streams impinging to create turbulence at their point to impact under conditions of temperature and pressure which permit reaction of said first and second reactive intermediates to produce a product; and, selecting said first and second solvents so that said product is insoluble in a mixture of said first and second solvents; and said jet streams impinging to create turbulence at their point of impact and each jet stream having sufficient linear velocity to achieve micromixing of said solutions followed by reaction of first and second reactive intermediates, followed by nucleation of said product and production of a crystalline product having small crystals of controlled particle size, wherein said crystals of said product meet bioavailability requirements, wherein said first reactive intermediate is selected from Ziprasidone free base or 5,8,14-triazatetracyclo[$10.3.1.0^{2,11}.0^{4,9}$]-hexadeca-2(11),3,5,7,9-pentaene free base, and said second reactive intermediate is selected from HCl or L-tartaric acid.

20. The process of claim 19, wherein said first reactive intermediate is Ziprasidone free base and said second reactive intermediate is HCl.

21. The process of claim 19, wherein said crystalline product is Ziprasidone hydrochloride monohydrate.

22. The process of claim 19, wherein said first reactive intermediate is 5,8,14-triazatetracyclo[$10.3.1.0^{2,11}.0^{4,9}$]-hexadeca-2(11),3,5,7,9-pentaene free base and said second reactive intermediate is a L-tartaric acid.

23. The process of claim 19 wherein said crystalline product is 5,8,14-triazatetracyclo[$10.3.1.0^{2,11}.0^{4,9}$]-hexadeca-2(11),3,5,7,9-pentaene (L)-tartrate.

24. A process for synthesis and crystallization of a pharmaceutical compound comprising contacting one or more jet streams of a solution in a first solvent of a first reactive intermediate and one or more jet streams of a solution in a second solvent of a second reactive intermediate, said jet streams impinging to create turbulence at their point of impact under conditions of temperature and pressure which permit reaction of said first and second reactive intermediates to produce a product; and selecting said first and second solvents so that said product is insoluble in a mixture of said first and second solvents, and said jet streams impinging to create turbulence at their point of impact and each jet stream having sufficient linear velocity to achieve micromixing of said solutions followed by reaction of first and second reactive intermediates, followed by nucleation of said product and production of a crystalline product having small crystals of controlled particle size, wherein said crystals of said product meet bioavailability requirements, wherein said first reactive intermediate is Voriconazole camphorsulfonic acid salt and said second reactive intermediate is a base and wherein said product is Voriconazole free base.

25. The process of claim 24 wherein said base is selected from sodium acetate, potassium acetate, sodium hydroxide, potassium hydroxide, sodium carbonate and sodium bicarbonate.

26. A process for synthesis and crystallization of a pharmaceutical compound comprising contacting one or more jet streams of a solution in a first solvent of a first reactive intermediate and one or more jet streams of a solution in a second solvent of a second reactive intermediate, said jet streams impinging to create turbulence at their point of impact under conditions of temperature and pressure which permit reaction of said first and second reactive intermediates to produce a product; and selecting said first and second solvents so that said product is insoluble in a mixture of said first and second solvents; and said jet streams impinging to create turbulence at their point of impact and each jet stream having sufficient linear velocity to achieve micromixing of said solutions followed by reaction of first and second reactive intermediates, followed by nucleation of said product and production of high surface area crystals of said product that meet bioavailability requirements wherein said first reactive intermediate is selected from Ziprasidone free base or 5,8,14-triazatetracyclo[10.3.1.0$^{2,11}$.0$^{4,9}$]-hexadeca-2(11),3,5,7,9-pentaene free base, and said second reactive intermediate is an acid, wherein said crystalline product is a pharmaceutically acceptable salt of Ziprasidone or 5,8,14-triazatetracyclo [10.3.1.0$^{2,11}$.0$^{4,9}$]-hexadeca-2(11), 3,5,7,9-pentaene selected from the group consisting of: hydrochloride, acetate, besylate, citrate, hydrobromide, D or L lactate, mesylate, succinate, sulfate, D or L tartrate, stearate and tosylate.

27. A process for synthesis and crystallization of a chemical compound comprising contacting one or more jet streams of a solution in a first solvent of a first reactive intermediate and one or more jet streams of a solution in a second solvent of a second reactive intermediate, said jet streams impinging to create turbulence at their point of impact under conditions of temperature and pressure which permit reaction of said first and second reactive intermediates to produce a product; and selecting said first and second solvents so that said product is insoluble in a mixture of said first and second solvents; and said jet streams impinging to create turbulence at their point of impact and each jet stream having sufficient linear velocity to achieve micromixing of said solutions followed by reaction of first and second reactive intermediates, followed by nucleation of said product and production of high surface area crystals of said product that meet bioavailability requirements, wherein said first reactive intermediate is a zwitterion and said second reactive intermediate is a base or an acid.

* * * * *